(12) United States Patent
Roe

(10) Patent No.: US 8,669,409 B2
(45) Date of Patent: Mar. 11, 2014

(54) REUSABLE OUTER COVER FOR AN ABSORBENT ARTICLE

(75) Inventor: Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 784 days.

(21) Appl. No.: 12/687,412

(22) Filed: Jan. 14, 2010

(65) Prior Publication Data

US 2010/0179495 A1 Jul. 15, 2010

Related U.S. Application Data

(60) Provisional application No. 61/144,883, filed on Jan. 15, 2009.

(51) Int. Cl.
*A61F 13/15* (2006.01)

(52) U.S. Cl.
USPC ................. 604/367; 604/385.29

(58) Field of Classification Search
USPC ........... 604/385.29, 367, 385.22, 385.21, 604/385.01; 428/101
See application file for complete search history.

(56) References Cited

U.S. PATENT DOCUMENTS

| | | | |
|---|---|---|---|
| 2,530,647 A | 11/1950 | Buchler | |
| 2,688,328 A | 9/1954 | Marcus | |
| 2,793,642 A | 5/1957 | Andruhovici | |
| 3,077,193 A | 2/1963 | Mann | |
| 3,496,259 A | 2/1970 | Guenther | |
| 3,560,292 A | 2/1971 | Butter | |
| 3,719,736 A | 3/1973 | Woodruff | |
| 3,735,424 A | 5/1973 | Maggio et al. | |
| 3,860,003 A | 1/1975 | Buell | |
| 3,911,173 A | 10/1975 | Sprague, Jr. | |
| 3,926,189 A | 12/1975 | Taylor | |
| 3,929,135 A | 12/1975 | Thompson | |
| 3,955,575 A | 5/1976 | Okuda | |
| 4,022,210 A | 5/1977 | Glassman | |
| 4,072,150 A | 2/1978 | Glassman | |
| 4,081,301 A | 3/1978 | Buell | |
| 4,116,892 A | 9/1978 | Schwarz | |
| 4,223,059 A | 9/1980 | Schwarz | |
| 4,265,245 A | 5/1981 | Glassman | |
| 4,284,454 A | 8/1981 | Joa | |
| 4,324,246 A | 4/1982 | Mullane et al. | |
| 4,326,302 A | 4/1982 | Lowe et al. | |
| 4,338,939 A | 7/1982 | Daville | |
| 4,342,314 A | 8/1982 | Radel et al. | |

(Continued)

FOREIGN PATENT DOCUMENTS

AU 642 386 10/1993
CA 2 103 537 2/1995

(Continued)

OTHER PUBLICATIONS

Internal Search Report, dated Mar. 29, 2010, 14 pages.

(Continued)

*Primary Examiner* — Tatyana Zalukaeva
*Assistant Examiner* — Benedict L Hanrahan
(74) *Attorney, Agent, or Firm* — Christian M. Best; Charles R. Ware

(57) ABSTRACT

Reusable cover for an absorbent article providing two or more features selected from maintaining skin condition, fitting a range of wearer shapes and sizes, being easily applied, providing conforming fit, and providing sustained fit.

20 Claims, 2 Drawing Sheets

(56) References Cited

U.S. PATENT DOCUMENTS

| | | |
|---|---|---|
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,773,906 A | 9/1988 | Krushel |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,936,840 A | 6/1990 | Proxmire |
| 4,955,880 A | 9/1990 | Rodriquez |
| 4,961,736 A | 10/1990 | McCloud |
| 4,961,737 A | 10/1990 | Orlando et al. |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,981,480 A | 1/1991 | Gaudet et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kjaergaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,807,371 A | 9/1998 | Toyoda et al. |
| 5,827,261 A | 10/1998 | Osborn et al. |
| 5,843,065 A | 12/1998 | Wyant |
| 5,843,267 A | 12/1998 | Cashaw et al. |
| H1788 H | 2/1999 | Christon et al. |
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 6,007,528 A | 12/1999 | Osborn |
| 6,010,491 A | 1/2000 | Roe et al. |
| 6,061,839 A | 5/2000 | Smolik |
| 6,120,487 A | 9/2000 | Ashton |
| 6,142,983 A | 11/2000 | Suprise et al. |
| 6,193,702 B1 | 2/2001 | Spencer |
| 6,207,738 B1 | 3/2001 | Zuckerman et al. |
| 6,229,061 B1 | 5/2001 | Dragoo et al. |
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,393,621 B1 | 5/2002 | Redwine et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |

(56) References Cited

U.S. PATENT DOCUMENTS

| | | |
|---|---|---|
| 6,482,191 B1 | 11/2002 | Roe et al. |
| 6,514,362 B1 | 2/2003 | Zuckerman et al. |
| 6,540,730 B1 | 4/2003 | Niedermeyer |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,579,273 B2 | 6/2003 | Dupuy |
| 6,605,071 B1 | 8/2003 | Gray et al. |
| 6,613,034 B2 | 9/2003 | Nozaki et al. |
| 6,623,466 B1 | 9/2003 | Richardson |
| 6,669,618 B2 | 12/2003 | Reising et al. |
| 6,680,422 B2 | 1/2004 | Roe |
| 6,716,441 B1 | 4/2004 | Osborne et al. |
| 6,764,477 B1 | 7/2004 | Chen et al. |
| 6,764,478 B2 | 7/2004 | Ashton et al. |
| 6,766,817 B2 | 7/2004 | da Silva |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,964,720 B2 | 11/2005 | Schneider et al. |
| 7,000,260 B2 | 2/2006 | Rajala et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,122,024 B2 | 10/2006 | Nakajima et al. |
| 7,166,095 B1 | 1/2007 | Coates |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,285,255 B2 | 10/2007 | Kadlec et al. |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Frank et al. |
| 7,494,483 B2 | 2/2009 | Beck et al. |
| 7,537,587 B2 | 5/2009 | Carstens |
| 7,576,019 B2 | 8/2009 | Bond et al. |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,771 B2 | 8/2010 | Autran et al. |
| 7,785,309 B2 | 8/2010 | Van Gompel et al. |
| 7,820,875 B2 | 10/2010 | Roe et al. |
| 7,833,211 B2 | 11/2010 | Mansfield |
| 7,914,507 B1 | 3/2011 | Magee |
| 7,993,322 B2 | 8/2011 | Brud et al. |
| 8,118,801 B2 | 2/2012 | Macura et al. |
| 8,158,043 B2 | 4/2012 | Gibson et al. |
| 2002/0010452 A1 | 1/2002 | Dupuy |
| 2002/0035747 A1 | 3/2002 | Kusibojoska et al. |
| 2002/0128619 A1 | 9/2002 | Carlbark et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0131382 A1 | 6/2005 | Brud et al. |
| 2005/0148974 A1 | 7/2005 | Datta et al. |
| 2005/0164587 A1 | 7/2005 | Melik et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakravarty et al. |
| 2006/0087053 A1 | 4/2006 | O'Donnell et al. |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0247599 A1 | 11/2006 | Mullen et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0125739 A1 | 5/2008 | Lodge et al. |
| 2008/0183148 A1 | 7/2008 | Labit et al. |
| 2008/0188822 A1 | 8/2008 | Lodge et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |

(56) References Cited

U.S. PATENT DOCUMENTS

| | | |
|---|---|---|
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0038738 A1 | 2/2009 | Nakamura |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0088713 A1 | 4/2009 | Norrby |
| 2009/0127742 A1 | 5/2009 | Qureshi et al. |
| 2009/0216209 A1 | 8/2009 | Ekstrom |
| 2010/0005570 A1 | 1/2010 | Rachman |
| 2010/0021037 A1 | 1/2010 | Zahniser et al. |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2011/0172628 A1 | 7/2011 | Roe et al. |
| 2012/0022481 A1 | 1/2012 | Roe et al. |
| 2012/0049404 A1 | 3/2012 | Gibson et al. |

FOREIGN PATENT DOCUMENTS

| | | |
|---|---|---|
| CA | 2 221 209 | 11/1996 |
| CA | 2 365 577 | 6/2003 |
| CN | 1505531 A | 6/2004 |
| CN | 1285727 A | 11/2006 |
| DE | 103 03 903 | 11/2003 |
| EP | 0 023 804 | 2/1981 |
| EP | 0 187 726 | 7/1986 |
| EP | 319314 | 6/1989 |
| EP | 0 811 362 A1 | 12/1997 |
| EP | 549988 | 6/1998 |
| EP | 796069 | 8/2000 |
| EP | 763353 | 6/2002 |
| EP | 2 106 775 | 10/2009 |
| FR | 2532337 A1 | 3/1984 |
| FR | 2606257 A1 | 5/1988 |
| GB | 112638 A | 1/1918 |
| GB | 2 440 314 | 1/2008 |
| JP | 55-37849 U | 9/1978 |
| JP | 57-138908 | 8/1982 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 61-168103 U | 10/1986 |
| JP | 62-110903 | 7/1987 |
| JP | 63-196701 A | 8/1988 |
| JP | 03-091325 | 1/1990 |
| JP | 04-7792 | 11/1990 |
| JP | 06-178795 | 1/1993 |
| JP | 6-63077 A | 3/1994 |
| JP | 3073695 | 9/2000 |
| JP | 2001/353183 A1 | 12/2001 |
| JP | 2002-95698 A | 4/2002 |
| JP | 2002-325786 | 11/2002 |
| JP | 2003-038564 | 2/2003 |
| JP | 2003-190213 A | 7/2003 |
| JP | 2005-6827 | 1/2005 |
| JP | 2005-111119 | 4/2005 |
| JP | 31-09189 | 5/2005 |
| JP | 2007-244506 | 3/2006 |
| JP | 2007-68654 A | 3/2007 |
| JP | 2008-055002 A | 3/2008 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-95/10992 | 4/1995 |
| WO | WO-95/16746 | 6/1995 |
| WO | WO-96/17572 | 6/1996 |
| WO | WO-96/24319 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 | 3/2008 |
| WO | WO-2008/120959 | 10/2008 |
| WO | WO-2008/142634 | 11/2008 |
| WO | WO 2010/053006 | 5/2010 |
| WO | WO 2010/111717 | 9/2010 |
| WO | WO 2010/113071 | 10/2010 |
| WO | WO 2010/134169 | 11/2010 |
| WO | WO 2010/135510 | 11/2010 |
| WO | WO 2011/047252 | 4/2011 |
| WO | WO 2011/047264 | 4/2011 |

OTHER PUBLICATIONS

E-mail from Elson Silva, dtd Jul. 26, 2010, re: Respecting Hydrology Science.
U.S. Appl. No. 12/687,528, filed Jan. 14, 2010, Donald Carroll Roe, et al.
U.S. Appl. No. 12/687,425, filed Jan. 14, 2010, Donald Carroll Roe, et al.
International Search Report dated Jun. 8, 2010, 7 pages.
All Office Actions, U.S. Appl. No. 12/687,528.
All Office Actions, U.S. Appl. No. 12/687,425.
www.gdiapers.com—Web pages dated Nov. 23, 2009.
www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants).
Data Sheet, p. V-17, from "Baby Diaper Design Update—1987", publication of Marketing Technology Service, Inc., product believed to be a product of Kao Corp. sold in Japan in 1986 or 1987.
US 5,583,910, 02/1994, Flint (withdrawn)

REUSABLE OUTER COVER FOR AN ABSORBENT ARTICLE

CROSS REFERENCE TO RELATED APPLICATION

This application claims the benefit of U.S. Provisional Application No. 61/144,883, filed Jan. 15, 2009, which is herein incorporated by reference in its entirety.

FIELD OF THE INVENTION

This disclosure relates to absorbent articles for the containment of bodily exudates, and more particularly to a reusable outer cover for absorbent articles.

BACKGROUND OF THE INVENTION

Absorbent articles, such as conventional taped diapers, pull-on diapers, training pants, incontinence briefs, sanitary napkins, and the like, offer the benefit of receiving and containing urine and/or other bodily exudates. Absorbent articles may be reusable. That is, the articles may be intended to be laundered or otherwise restored for multiple uses. In some instances, portions of an absorbent article may be reusable and other portions may be disposable. For example, an absorbent article may comprise a reusable outer cover and a disposable insert which is discarded after soiling.

Ideally, an absorbent article should maintain skin condition and provide sizing for a range of wearer shapes and sizes, ease of application, conforming fit, and sustained fit. Achieving combinations of these characteristics has been difficult in reusable absorbent articles. While progress has been made in providing breathable, stretchable disposable absorbent articles, many of the materials and methods used to manufacture disposable absorbent articles are ill-suited for adaptation to reusable absorbent articles. For example, breathability may reduce over-hydration and associated "diaper rash" and erythema commonly associated with regular use of an absorbent article. In disposable absorbent articles, good breathability can be achieved using microporous films or films which are apertured over small areas to permit water vapor transmission across the films, without concurrent passage of liquids, such as urine. However, microporous films do not provide the stretch required for sizing, ease of application, conforming fit, and sustained fit in a reusable outer cover for an absorbent article. Similarly, the extension of aperturing to large areas of the outer cover may lead to increased leakage of liquids, such as urine, or the liquid components of other exudates such as feces and menses.

In light of the difficulty in balancing the competing, desirable attributes in a reusable outer cover for an absorbent article, many reusable outer covers perform only basic functions, such as exudate containment. For example, a reusable outer cover for an absorbent article may use a relatively thick polymeric film to reduce leakage, at the expense of sizing, fit, and breathability.

There remains a need for a reusable outer cover for an absorbent article which provides acceptable performance in more than one aspect maintaining skin condition and providing sizing for a range of wearer shapes and sizes, ease of application, conforming fit, and sustained fit.

SUMMARY OF THE INVENTION

What is claimed is a reusable outer cover for an absorbent article having a front region, a back region, and a crotch region disposed longitudinally between the front region and the back region, and a wearer-facing surface disposed opposite a garment-facing surface. The reusable outer cover may comprise an inner layer defining the wearer-facing surface of the outer cover and an outer layer defining the garment-facing surface of the outer cover; a first longitudinally extending edge and a second longitudinally extending edge laterally spaced from the first longitudinally extending edge; a first elastic leg band adjacent the first longitudinally extending edge; a second elastic leg band adjacent the second longitudinally extending edge; a first laterally extending edge and a second laterally extending edge longitudinally spaced from the first laterally extending edge; a first elastic waist band adjacent the first lateral end edge; a second elastic waist band adjacent the second lateral end edge; a first side panel having a distal end portion extending laterally outward from the first longitudinally extending edge; a second side panel having a distal end portion extending laterally outward from the second longitudinally extending edge; and an anchoring band attached to at least one of the inner layer and the outer layer at two or more attachment points between the first and second side panels proximate a laterally extending edge corresponding to the back region of the absorbent article, wherein the anchoring band is free to move relative to the inner and outer layers between the attachment points. The outer cover may have a WVTR of at least 1200 $g/m^2/24$ hr and a Whole Product Back Extension of at least 15% under an applied force of 5N.

The inner layer and the outer layer may be apertured. The inner layer may have a higher modulus of elasticity than the outer layer. The inner layer may be hydrophobic. The outer layer may be hydrophobic, and the inner layer may be more hydrophobic than the outer layer.

The outer layer may be a woven fabric. The outer layer may be made from a material selected from the group consisting of cotton, wool, bamboo, hemp, silk, rayon, polyester, nylon, Lycra, Spandex, breathable waterproof materials with microscopic pores smaller than a water droplet but larger than a water vapor molecule, fabrics comprising microencapsulated phase-change polymer materials, fiber-based moisture wicking systems, and combinations thereof. The outer layer may have a basis weight from 0.09-0.15 $gram/in^2$.

A reusable outer cover for an absorbent article may have a WVTR of at least 1200 $g/m^2/24$ hr, or 3000 $g/m^2/24$ hr, and a Whole Product Back Extension of at least 15% under an applied force of 5N. The outer cover may have a WVTR of less than 15,000 $g/m^2/24$ hr, or 10,000 $g/m^2/24$ hr. The outer cover may a Whole Product Back Extension of less than 150 mm, or 100 mm, under an applied force of 5N. The outer cover may have an unload force of at least 1.0N, or 2.0 N, at 25% extension in the Whole Product Back Extension test.

A reusable outer cover for an absorbent article may have a Whole Product Back Extension of at least 15% under an applied force of 5N and an Outer Cover Extension Force at 25% extension of less than 10N, or 5N. The outer cover may have an Outer Cover Extension Force at 50% extension of less than 10N, or 5N.

DETAILED DESCRIPTION OF THE INVENTION

Figure 1:
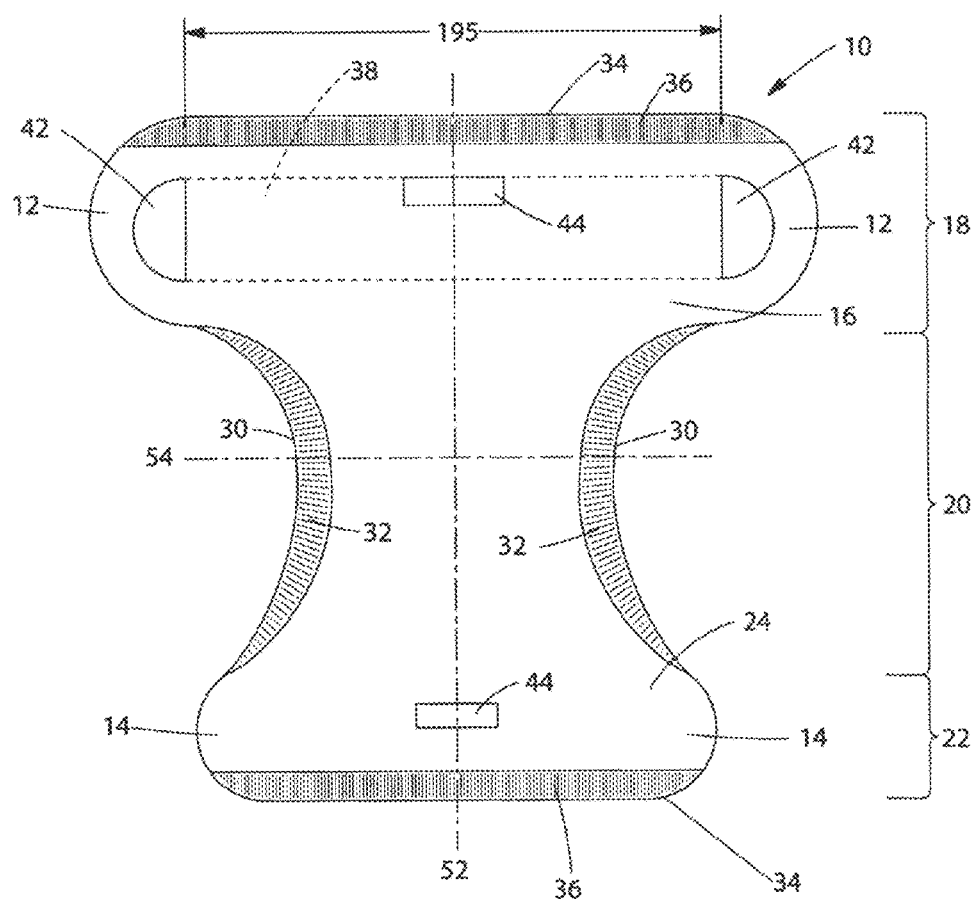
FIG. 1 is a plan view of an exemplary reusable cover.

The term "disposable," as used herein in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

The term "absorbent article" as used herein refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like. Absorbent articles include reusable absorbent articles.

The term "reusable," as used herein means that a referenced material, component, or all of an absorbent article is configured to be restored and/or reused for more than one usage cycle (e.g., a diaper change). In some reusable absorbent articles, part, or parts, or substantially all, or all of the articles may be launderable or laundering resistant, as defined and described herein. Another part or parts of a reusable absorbent article may not be launderable or laundering resistant. For example, some parts of a reusable absorbent article may be discarded after soiling and replaced with a new part, such as an absorbent insert which is used with a reusable outer cover.

The term "launderable," as used herein means that a referenced material, component, or all of an absorbent article is configured to withstand a large number (e.g. at least 10, in some embodiments up to 50, in other embodiments more than 50) of cycles of machine washing and machine drying (as defined by AATCC Test Method 124-2001, with modifications as described below), without significant degradation to the appearance or performance of the article that would render it unsuitable for its intended functionality or use. Since hand-washing and line-drying are typically less stressful on an absorbent article than machine washing and machine drying, it is expected that a material, component, or article that is machine washable and machine dryable should also be hand-washable and hand-dryable for at least as many cycles. As an example, a reusable absorbent article may include an outer cover that is launderable. Launderable articles are designed to be suitable for use after many washings, similar to types of clothing.

The term "laundering resistant," as used herein means that a referenced material, or component, or all of an absorbent article is configured to withstand a small number (e.g. at least one, in some embodiments up to five, in other embodiments more than five) of cycles of machine washing and machine drying (as defined by AATCC Test Method 124-2001, with modifications as described below), without significant degradation to the appearance or performance of the article that would render it unsuitable for its intended functionality and/or use. As an example, a reusable absorbent article may include an outer cover that is laundering resistant. Laundering resistant articles generally experience degradation after fewer laundering cycles than launderable articles.

The term "wearer-facing," as used herein means the side of an article or component of an article that is nearest the wearer when the article is fitted to a wearer as intended for normal use. The term "garment-facing," as used herein means the side of an article or component of an article that is opposite to the wearer-facing surface and furthest from the wearer when the article is fitted to a wearer as intended for normal use.

As used herein, the term "hydrophilic" describes surfaces which are wettable by aqueous fluids (e.g., aqueous body fluids) deposited on these surfaces. Hydrophilicity and wettability are typically defined in terms of contact angle and the strike through time of the fluids, for example through a non-woven fabric. This is discussed in detail in the American Chemical Society publication entitled "Contact angle, wettability and adhesion", edited by Robert F. Gould (Copyright 1964). A surface is said to be wetted by a fluid (i.e., hydrophilic) when either the contact angle between the fluid and the surface, is less than 90°, or when the fluid tends to spread spontaneously across the surface, both conditions normally co-existing. Conversely, a surface is considered to be "hydrophobic" if the contact angle is greater than 90° and the fluid does not spread spontaneously across the surface of the fiber. Contact angle is measured using a Kruss Drop Shape Analysis System, Model DSA10-Mk2, as available from Kruss USA in Charlotte, N.C.

"Nonwoven" refers herein to a fibrous structure made from an assembly of continuous fibers, coextruded fibers, non-continuous fibers and combinations thereof, without weaving or knitting, by processes such as spunbonding, carding, melt-blowing, airlaying, wetlaying, coforming, or other such processes known in the art for such purposes. The process for incorporating a fiber into a substrate may be selected based upon the sorts of component materials used and the desired properties of the substrate web. The nonwoven material may comprise one or more layers of fibrous assemblies, wherein each layer may include continuous fibers, coextruded fibers, non-continuous fibers and combinations thereof.

The primary function of absorbent articles is to absorb and contain bodily exudates from the wearer. In order to accomplish this function, the article must also be capable of fitting and being applied to the wearer, maintaining the relative location of the absorbent material to the exudate release locations on the wearer's anatomy, maintaining contact of any gasketing systems with the wearer's body, and maintaining the physical integrity of the article while in use. The article should also cover the region of the body to which the absorbent article is applied to provide confidence of exudate containment and desired modesty levels (i.e. both area of coverage and opacity). Additionally, the absorbent article should prevent or minimize any negative side effects of wearing the article for its intended purpose. For example, the article should provide comfort in any body position, avoid indenting or marking the wearer's skin, and over-hydration of the wearer's skin, and should not inhibit the movement of the wearer. In conventional one-piece absorbent articles, these functions must all be performed by a single composite element. However, in absorbent articles provided as separate elements— i.e., a reusable outer cover and replaceable insert cores— some of these functions may be separated between the two elements. For example, in the latter product form, the outer cover may, or may not, be fluid impermeable as the insert may comprise a self-contained absorbent assembly including an impermeable layer and a gasketing system.

In some embodiments, the outer cover of a high-performance absorbent article performs at least two of several key functions, including maintaining skin condition; fitting a wide range of wearers; being easy to apply; providing a conforming fit that adapts to wearer position and motion; and providing sustained fit to maintain the relative position of the article, especially the absorbent core or insert, with respect to the wearer's anatomy. In other embodiments, the outer cover may perform all of these functions.

Structure

An exemplary reusable outer cover for an absorbent article is shown in FIG. 1. Reusable cover 10 is shown with wearer-facing side 16 up. Reusable cover 10 has longitudinal centerline 52 and lateral centerline 54. Reusable cover 10 has front region 22, crotch region 20, and back region 18. When reusable cover 10 is fitted to a wearer as intended for normal use, front region 22 generally corresponds to the wearer's front or stomach, crotch region 20 generally corresponds to the area between the wearer's legs, and back region 18 generally corresponds to the wearer's back, at approximately hip level or above. Reusable cover 10 has back side panels 12, and may also have front side panels 14. As shown, back side panels 12 are somewhat larger than front side panels 14, however, front side panels 14 may be the same size or larger than back side panels 12 in some embodiments. In some embodiments, reusable cover 10 has only front side panels 14 and no back side panels 12. Front side panels 14 and/or back side panels 12, if present, may be integral to the main body of reusable outer cover 10, or may be discrete pieces joined to the main body of resusable outer cover 10. In some embodiments, front side panels 14 and/or back side panels 12 may be formed from at least part of the laterally distal area of at least one of the waist regions, rather than a distinct part of reusable outer cover 10. While the present disclosure refers to front fastenable wearable absorbent articles, the present disclosure also contemplates alternate embodiments of wearable absorbent articles, wherein the wearable absorbent articles are rear-fastenable, or side-fastenable.

Reusable cover 10 has an inner layer 24 which makes up at least part of wearer-facing side 16, and an outer layer 26 (not shown in FIG. 1), which makes up at least part of garment-facing side 28. Reusable cover 10 has a pair of laterally opposed, longitudinally extending side edges 30, which are curved or hour-glass shaped in the exemplary embodiment of FIG. 1. In some embodiments, longitudinally extending side edges 30 may be straight, or substantially straight, or may have a curvature different from that depicted in FIG. 1. Each longitudinally extending side edge 30 has an elastic leg band 32. Reusable cover 10 also has a pair of longitudinally opposed, laterally extending edges 34, and each laterally extending edge 34 has a waist band 36. One of the laterally extending edges 34 corresponds to back region 18, and the other laterally extending edge 34 corresponds to front region 22. In some embodiments, reusable cover 10 may have only a back waistband, or only a front waistband, instead of having waistbands at both laterally extending edges 34.

Anchoring band 38 is shown disposed between inner layer 24 and outer layer 26, and may be attached at attachment points 40 at or laterally inward of each of back side panels 12, or, if back side panels 12 are not present and in some embodiments with back side panels 12, at or laterally inward of longitudinally extending edges 30. Between attachment points 40, anchoring band 38 is free to move relative to inner layer 24 and outer layer 26. As such, anchoring band 38 may provide fitment forces to help hold reusable cover 10 in place on a wearer, even as the weight of the absorbent article increases and shifts as the absorbent article is filled with exudates. For example, the anchoring band, or the combination of the anchoring band and the outer cover adjacent the anchoring band, may have a higher extension force or unload force at a given degree of extension than the region of the outer cover not associated with the anchoring band. Two attachment points 40 are shown, however, there may be one or more additional attachment points along anchoring band 38. Some embodiments may have no anchoring band. In some embodiments, the outer cover is made of only one layer. In such an embodiment, an anchoring band may be attached to the inside or outside of the outer cover. In other embodiments, the outer cover may comprise a region having properties different from the remainder of the outer cover, instead of or in addition to a distinct anchoring band. In some other embodiments, anchoring band 38 may be attached to the outer cover, or an element thereof, across all or substantially all of its area.

Outer cover 10 may include fasteners 42 for attaching back side panels 12 to front side panels 14 or to garment-facing side 28 of front region 22 or to panel 46 (i.e., a landing zone). Outer cover 10 may also include insert attachment points 44 for connecting an absorbent insert (not shown). For example, outer cover 10 may not provide significant absorptive capacity, and may require an absorbent insert to take up and contain any significant amount of liquid exudates, such as urine, or liquid components of exudates such as feces and menses. Attachment points 42 may comprise fastening elements, which may the same as or different than fasteners 42.

Figure 2:
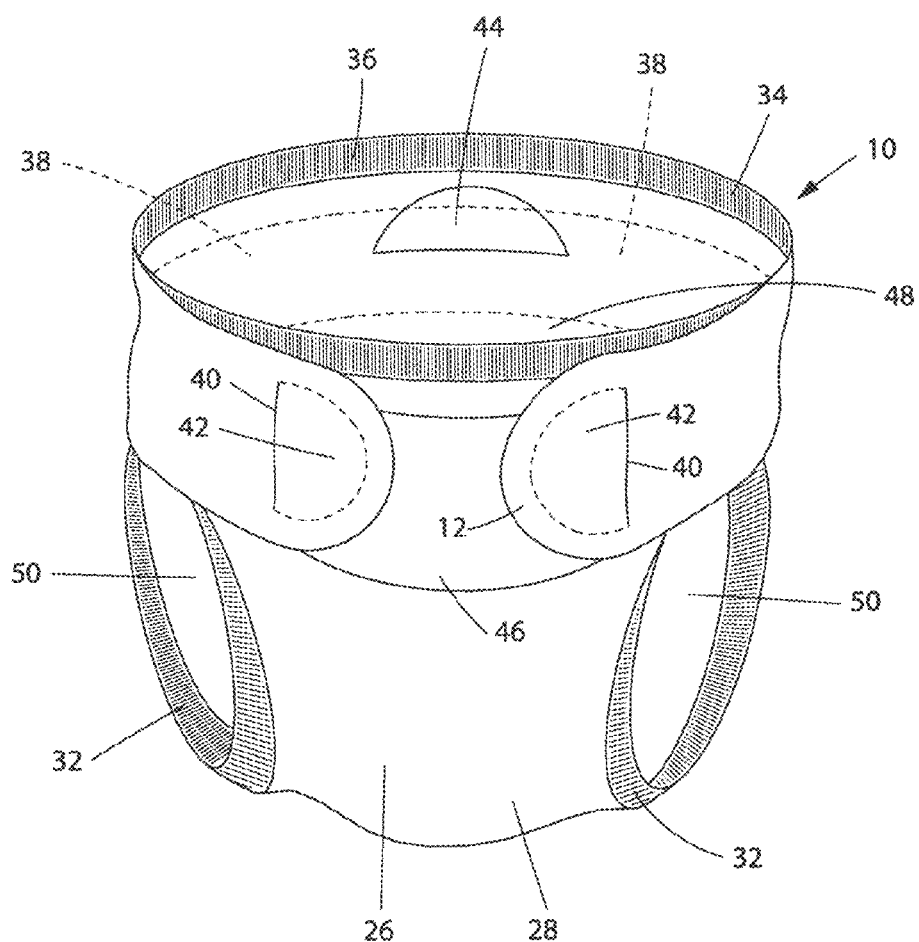
FIG. 2 is a perspective view of an exemplary reusable cover.

FIG. 2 shows outer cover 10 as it would be configured when fitted to a wearer for normal use, with waist opening 48 and leg openings 50. Additional details about the structure and materials of outer cover 10 are provided below.

Skin Condition

A well-known primary factor in poor skin condition associated with the use of absorbent articles is over-hydration of the skin caused by high localized humidity between the absorbent article and the wearer's skin. Over-hydrated skin may exhibit erythema (redness), diaper dermatitis, and may be less resistant to abrasion (i.e., from a lower tensile strength). An outer cover may have a minimum breathability, or Water Vapor Transmission Rate (WVTR) as measured by the Mocon test described below, to allow sufficient water vapor from urine and/or sweat to leave the interior of the article, maintaining the skin hydration at a lower level. The outer cover may have a WVTR of at least about 1200 $g/m^2/24$ hr, or a WVTR of at least about 3000 $g/m^2/24$ hr. Higher WVTRs may be helpful when the ambient conditions are higher in temperature and/or humidity, when the wearer is more active (e.g., perspires more), and/or when the diaper has a higher loading of urine or other liquid exudates (e.g., during overnight use or when the user is a "heavy wetter"). Thus, a WVTR of at least about 1200 $g/m^2/24$ hr may indicate a serviceable outer cover in typical use, while a WVTR of at least about 3000 $g/m^2/24$ hr may indicate a serviceable outer cover under more challenging conditions. In certain instances, too high a breathability can have negative effects, such as moisture condensation, on the garment-facing surface of the article or on clothing. Outer covers may have a WVTR of less than about 15,000 $g/m^2/24$ hr, or even 10,000 $g/m^2/24$ hr, to help prevent this phenomenon. A lower maximum WVTR indicates a serviceable outer cover under challenging conditions, such as lower ambient temperatures, where escaping water vapor may generate more condensation than at relatively higher ambient temperatures.

In the past, some outer covers for reusable absorbent articles have been made of relatively thick films with very low water vapor transmission rates, often well below 1000 $g/m^2/24$ hr (see Examples 5, 9, and 10, below). One method of producing an outer cover for a reusable absorbent article with a more robust WVTR is to use a microporous film. However, microporous films exhibit minimal elastic extension and recovery. A breathable, stretchable outer cover may be desirable. For example, a stretchable woven fabric may be used as the outer cover. A porous, stretchable woven fabric allows air and water vapor to pass through. A higher WVTR may also be achieved by mechanically aperturing the outer cover, such that air and water vapor can traverse the thickness of the outer cover. Liquid penetration can then be managed by controlling the aperture or pore size or by providing inner layer 24 of the outer cover 10, wherein at least one of inner layer 24 and outer layer 26 is hydrophobic.

A breathable, stretchable outer cover with reduced liquid penetration may also be provided by employing more than one layer of a stretchable woven fabric as the outer cover. In some embodiments, inner layer 24 and outer layer 26 may have the same or similar properties, and the duplication of the material may create a break in capillary continuity, therefore providing more resistance to liquid penetration. In some embodiments, inner layer 24 and outer layer 26 are different. For example, outer layer 26 may be a soft, extensible layer with pleasant tactile and aesthetic properties, while inner layer 24 is a hydrophobic layer with desirable moisture barrier properties. Inner layer 24 may have smaller pores than outer layer 26, and, therefore, transmit less water.

Launderable outer cover materials may include any natural or synthetic materials known in the diaper, pant, underwear, performance clothing, sport clothing, or general clothing or textile arts. These materials may include natural materials such as cotton, wool, bamboo, hemp, silk, rayon, and the like, as well as blends of these materials with synthetic fibers. Exemplary synthetic materials suitable for use in launderable outer covers may include polyolefins, polyester, nylon, Lycra, Spandex, or other elastomers; breathable waterproof materials with microscopic pores smaller than a water droplet but larger than a water vapor molecule, such as GORE-TEX® (W. L. Gore & Associates, Inc., Elkton, Md.); fabrics comprising microencapsulated phase-change polymer materials such as Outlast ComforTemp fabrics (Outlast Technologies, Boulder, Colo.—see U.S. Pat. No. 6,514,362 and U.S. Pat. No. 6,207,738, for example); fiber-based moisture wicking systems, such as COOLMAX® (INVISTA, Wichita, Kans.); and the like. These materials may include at least one fiber-based material, such as a fabric or woven or nonwoven web. However, outer cover 10 may additionally comprise a film layer to provide enhanced liquid penetration resistance or elastic properties to the outer cover. Elastic properties can be added or enhanced via the addition of other materials to the outer cover, including elastic strands, bands, scrims, and the like.

Launderable materials may be formed in any known weave or fabric form, including birdseye fabric; terry; fleece; flannel; knits; stretch knits; sherpa; suedecloth; microfleece; satin; velour; Burley knits; and a dual-surface, tight-construction fabric such as Polartec® Windpro® (Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastic fibers. Specific suitable examples for launderable outer cover materials include, but are not limited to, jersey knits of blends of: rayon (93%) and spandex (7%) fibers; modal (94%) and spandex (6%) fibers; cotton and spandex fibers; and bamboo and spandex fibers. Launderable materials may have basis weights of about 0.09-0.15 gram/in.$^2$ per layer, or other basis weights (basis weight may be measured using EDANA/INDA method WSP 130.1 (05), except in step 4(b), use a sample size of 25 mm×20 mm, and disregard step 5.2).

In some instances, outer covers that are laundering resistant may be sufficiently inexpensive to allow them to be discarded without issues of cost or conscience if soiled extensively or damaged, while still providing some benefit in terms of reducing environmental impact from product disposal. Laundering resistant outer cover materials may include any of the materials described herein, including one or more materials contemplated for use in launderable or disposable outer covers. If materials for use in launderable outer covers are selected, typically less expensive, lower quality (e.g., lower basis weight, less optimal fiber quality) versions may be employed, to form outer covers that are laundering resistant. If materials for use in disposable outer covers are selected, higher basis weights and/or quality of materials may be appropriate. Blends or laminates of such materials are also contemplated for laundering resistant outer covers.

For outer covers that are laundering resistant, materials may include any natural or synthetic nonwoven web and/or film materials known in the diaper or pant arts. Laundering resistant materials of which an outer cover may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of an outer cover. An outer cover according to the present disclosure may further include films in at least some areas, as, for example, films of polypropylene and/or polyethylene.

Non-limiting examples of fibers, nonwovens and laminates of nonwovens and films that might be considered for use as laundering resistant outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Fit Range and Ease of Application

For wearable articles, such as diapers, requiring the caregiver or wearer to fasten the back and front sides of the article together around the wearer's lower torso, the back waist region of the article may extend at least a minimum amount under a tension representative of what a caregiver might apply to the side panels, or ears, in the rear of the article while applying the article to a wearer. The induced extension provides a wider potential fit range by accommodating larger and smaller wearers. The extension may also provide an easier application to the wearer by enabling a caregiver to more easily align the back and front portions of the article in a secure, comfortable, and aesthetically pleasing manner prior to engaging the fastening system. Articles that are pre-formed in a pant-like configuration prior to application to a wearer may provide at least a minimum level of extension under forces applied to the article during application in order to allow the article to be pulled up over the wearer's thighs and buttocks regions. In some embodiments, the back waist region of the article may have a relative percent extension (i.e., change in length over original length) of at least about 15%, or at least about 20%, under an applied force of 5N in the Whole Product Back Extension test described below. A greater whole product back extension may allow the outer cover to fit a larger range of user sizes than a lower whole product back extension, while a lower whole product back extension may allow for a closer, more tailored fit to a narrower range of user sizes. Pant-type articles may require greater back waist extension at 5N or 10N to allow the article to be pulled up over the wearer's hips and buttocks. For example, a pant-type article may have a Whole Product Back Extension of at least about 40% at 5N and at least about 70% at 10N.

In addition to the relative extension, an outer cover may allow a minimum absolute Whole Product Back Extension in order to provide a minimum size accommodation through extension. In some embodiments, the back waist region of the article may extend at least about 25 mm, or at least about 50 mm, under 5N applied lateral force in the Whole Product Back Extension Test. In some embodiments, it may be desirable to limit the maximum absolute back waist extension of the article in order to prevent the waist region from extending too much, which might lead to sagging in use and/or a "fit" that is too large for smaller wearers. In such embodiments, the back waist region of the article may extend no more than about 150, or 125 or even 100 mm, under 5N applied lateral force in the Whole Product Back Extension Test. The values described above for absolute Whole Product Back Extension are appropriate for a diaper sized for users approximately 22-37 pounds (approximately 10-17 kg). The absolute values for Whole Product Back Extension may be somewhat smaller for an absorbent article for smaller users, and may be significantly larger for an absorbent article for larger users, such as incontinent adults.

Conforming Fit

The buttocks region of some humans expands about 50% in width during the process of moving from a standing position to a squatting position. In order to provide a conforming fit in all wearer body positions, the outer cover may extend 50% in the lateral direction under no more than 10 N, or 5 N, of applied force. If the outer cover comprises more than one layer of material, whether the multiple layers are bonded together or not, it is the extension of the entire composite that may help provide a conforming fit. For example, an article may have an outer cover having two layers, one of which meets the above extension criteria if tested separately and one which does not. Since both layers would be present during usage of the article, it is their extension performance as a combined outer cover that the wearer will experience. Therefore, the Outer Cover Extension test should be performed on the composite. In some embodiments, the outer cover may only have these properties in the back portion of the article.

In contrast, the Whole Product Back Extension Test, discussed above and described below, is performed on all elements of the fully assembled outer cover, which may include a waistband, leg bands, anchoring bands, etc., and will reflect the methods and structures for joining those elements. The outer cover extension data indicates how the outer cover will expand with the wearer as the wearer moves, and more particularly, when the wearer squats. The Whole Product Back Extension Test reflects size and fit, and may provide insight into differences in the ease of applying an article to a wearer.

Sustained Fit

During use, an absorbent article experiences a variety of downward-directed forces induced by gravity and/or wearer motions. These forces generally increase as the time the wearer has worn a particular article increases, driven by the addition of mass to the article in the form of urine and/or other excrement. In order to counter these forces and maintain adequate sustained fit, the article should retain at least about 1.0N "unload" force at 25% extension in the Whole Product Back Extension test. In some embodiments, the article should retain at least about 1.5N, and more preferably at least about 2.0 N, "unload" force at 25% extension in the Whole Product Back Extension test. The unload forces predict how well the absorbent article will fit when the absorbent article is "loaded," as with urine, feces, menses, etc., and during user movement. The amount of load the product can withstand without undesirable changes in fit or performance will increase with increasing unload forces.

A reusable outer cover may include an anchoring band to help enhance the fit and securement of the outer cover about the waist of a wearer. Anchoring band 38, as shown in FIG. 1, may include an elastic or elasticized strip or band of material, affixed to outer cover 10 at locations proximate to its rearward corners or proximate to back side panels 12. Thus, anchoring band 38 may be partially or substantially force-decoupled along its lateral length from inner layer 24 and outer layer 26, via attachment to outer cover 10 only by the ends of anchoring band 38, or only at a limited number of selected intermediate lateral locations along anchoring band 38. For example, anchoring band 38 might be attached to outer cover 10 only at the ends of anchoring band 38. In another example, anchoring band 38 might be attached to outer cover 10 only at the ends and at the lateral center of anchoring band 38. This substantially force-decoupled arrangement allows anchoring band 38 and surrounding portions of outer cover 10 to stretch and move substantially independently of one another, which may promote better fit and comfort. In another example, however, anchoring band 38 may be an elastic band, strip or strap laminated with or otherwise affixed to inner layer 24 or outer layer 26 along substantially the entire length of anchoring band 38.

When strained laterally by application to the wearer, anchoring band 38 may serve to provide, or supplement, extension or unload forces in the article about the wearer's waist, thereby tending to draw waist opening 48 snug, enhancing fit and enhancing securement of the wearable absorbent article about the wearer's waist. The elastic modulus of anchoring band 38 may be higher than the elastic modulus of the surrounding, adjacent, or coextensive outer cover materials.

An anchoring band, or system of one or more anchoring band members, may have any additional features described in, for example, co-pending U.S. Patent Application Publication Nos. 2008-0004591; 2008-0004589; 2008-0188822; 2008-0125739; 2008-0004593; 2008-0004592; 2008-0004586; 2008-0004587; 2008-0004590; 2008-0004582; 2008-0004583; 2008-0004584; 2007-0287983; 2008-0015537; 2007-0287982; 2009-0069779; 2009-0069772; 2009-0069782; 2009-0069773; 2009-0069774; 2009-0069775; 2009-0069778; 2009-0069777; and 2009-0069781.

In another example, instead of, or in addition to, being oriented substantially laterally as suggested by the depicted location of anchoring band 38 in FIGS. 1 and 2, one or more members forming anchoring bands may be oriented diagonally or in a curvilinear manner between the longitudinal and lateral directions. For example, a pair of diagonal anchoring bands may have respective waist ends thereof affixed at a location area proximate to corners of outer cover 10 and/or back side panels 12, and respectively extend toward both the lateral and longitudinal center of outer cover 10. The respective center ends of the diagonal anchoring bands may be affixed to outer cover 10 at locations proximate the lateral center of outer cover 10, and the diagonal anchoring bands may be either force-decoupled or force-coupled to the chassis along the lengths of the bands. In an example wherein an insert is connected to an anchoring band for additional longitudinal support, diagonal anchor bands may serve to provide supplementary longitudinal tension along outer cover 10, providing supplemental longitudinal support within outer cover 10.

While each of the functions described above individually contributes to a serviceable outer cover for a reusable absorbent article, some high-performance absorbent articles may have adequate performance in more than one of these functions. A given wearable article may perform all of these functions at least at a minimum acceptable level. However, embodiments are contemplated where this may not be feasible due to material or cost limitations. Exemplary, non-limiting, combinations of properties that may be of interest to consumers include, but are not limited to, maintaining skin condition and sizing or ease of application. Alternatively, the article may provide adequate sizing/ease of application and sustained fit. Another combination of interest is adequate conforming fit and sustained fit.

EXAMPLES

Data on the above properties is generated for both Launderable (Example 1) and Laundering Resistant (Example 2) exemplary embodiments of absorbent articles. The same data is generated, for comparative purposes, on a number of outer cover products available on the market that are intended to be used with either washable or disposable inserts. All products are tested in an "as-purchased" condition without any insert. Example 4 (gDiaper) is tested without the separately attachable insert liner. This data is presented in Table 1.

Example 1 is a launderable outer cover having an outer layer, an inner liner, left and right side leg bands, front and back waist bands, an anchoring band, a front landing zone, two ear fastening elements adapted to fasten releasably to the landing zone, front and back ear stiffeners, and two insert fastening elements. The outer layer forms the largest portion of the garment-facing surface of the resulting outer cover and is soft and stretchable. The outer cover comprises a jersey knit material comprising 95% Modal and 5% Lycra, available from Koshtex.com.

The anchoring band provides an anchoring line of tension below the back waist band and over the top of the wearer's buttocks and hips. The anchoring band has a higher elastic tension (a higher unload force) than the outer layer when worn by a wearer in a stretched condition—i.e., the anchoring band has a higher elastic modulus and lower elastic hysteresis than the outer layer. The elastic modulus is the average slope of the stress-strain curve on the first pull in the Hysteresis Test. The elastic hysteresis is the difference in the force, at a given extension and in the first cycle, between the load and unload forces. The anchoring band comprises a 90%/10% Spandex/knit blend available as "blue spandex" from Rose City Textiles.

The inner liner covers the anchoring band and ear stiffeners, provides a surface to which to attach the insert fastening elements, and provides a hydrophobic surface at least in the crotch and front regions of the outer cover to prevent or resist urine penetration to the outer layer. The inner liner is stretchable in at least the back portion of the outer cover in order to allow the outer cover to stretch to comfortably fit a wide range of wearers. In this example, the inner liner comprises a front piece and a back piece. The front piece extends from the front waist edge of the outer cover through the crotch region 68% of the length of the outer cover. The front piece is resistant to water permeation and comprises 90% Nylon Tricot, 10% Spandex, available as Sportek FM-60 DWR. The back piece comprises a 94% polyester, 6% Spandex Brazil knit fabric available as pattern 23221 from Telio & Cie.

The front landing zone and ear fastening elements are adapted to releasably and securely fasten to one another. The landing zone is disposed near the front waist edge of the outer cover and comprises the loop component of a hook and loop fastening system. The ear fastening elements are disposed on the wearer-facing surface of the outer cover in the back ear regions—i.e., the laterally distal portions of the back waist region of the outer cover—and comprise the hook component of a hook and loop fastening system.

The leg and waist bands are elastic, soft, and comfortable for the wearer. The leg and waist bands comprise an outer tube layer of a soft extensible fabric and an inner elastic component. The tube layer fabric in this embodiment comprises the same material as the outer layer, but in a different, aesthetically complementary color. The elastic component comprises ¼"-⅜" natural elastic, available from Lea & Sachs, Inc. as Item Number 301800.

The front and ears comprise stiffening elements disposed between the outer layer and inner liner in the laterally and longitudinally distal corners of the outer cover. The stiffening elements resist folding or buckling of the ears and/or fastening elements to provide an easier application process for the wearer or a caregiver, improved fastening security, and an improved fit of the outer cover on the wearer. The stiffening elements comprise medium weight woven interfacing available as Pellon Shape-Flex All purpose woven fusible interfacing SF101 100% Cotton from Joann Fabric, Cincinnati, Ohio.

The outer cover also provides means by which an absorbent insert may be releasably affixed thereto in order to provide a complete and functional absorbent article for the wearer's use. An insert fastening element comprising the loop component of a hook and loop fastening system is disposed in each of the front and back waist regions on the wearer-facing surface of the outer cover. The insert fastening elements are Touchtape Hook and loop or Aplix 960 hooks with Touchtape loop.

The following provides a brief description of various steps that may be used to assemble the launderable outer cover.

The outer layer and inner liner, or components thereof, are cut to shape using a pattern, the dimensions of which are at least ⅛ inch larger than the intended finished article to allow for seams. Using a sewing machine, the landing zone loop is zigzag stitched to the outside of the outer cover. Thread used is Coats and Clark 63% Polyester 37% Cotton.

A 255 mm anchoring band is straight stitched on the left and right sides to the wrong side of the back inner layer, leaving an approximately 0.125 inch seam allowance on each side. The anchoring band is centered in the cross direction, and is placed approximately 12 mm from the fabric edge. The back inner layer is turned over and straight stitched down the center of the colored arch landing zone on the right side of the fabric to hold the anchoring band in place during wear.

Each portion of the liner has a waist edge and a linear inner lateral edge longitudinally opposed to the waist edge. Place the front and back inner liner components in a face-to-face relationship, with the right side of the back portion facing the right side of the front portion and with the inner edges of the liner portions aligned in a coterminous manner. Using a serger, serge the laterally outboard regions of the inner edges together using Woolly Nylon thread available from Beacon Fabric & Notions Item #240, leaving approximately 1.5 inch unseamed in the center. This unseamed region forms a hole by which the outer cover may be turned "right side in" when completed. The composite inner liner is opened and laid flat.

The Pellon medium weight woven interfacing stiffening element is added to ears of interior and exterior front and back (total of 8 pieces of pre-cut Pellon per cover) to wrong side of fabrics. The stiffening elements are the same size and shape as the ear. A stiffening element is fused to the wrong side of each the back ears of the outer cover. Fusing is done with an electric iron (model Black and Decker "the Classic" Steam Iron with 1-7 settings at setting 5.5). A stiffening element is fused to the wrong side of each the front ears of the outer cover in the same manner.

The leg bands have a front end which will terminate in the front of the finished outer cover and a back end which will terminate in the back of the finished outer cover. The fabric tube components of the leg band are cut to a length of 370 mm. Each leg band fabric tube layer is folded in half along its longitudinal axis and pressed with a heated iron to make a crease. A 250 mm long piece of the elastic component is inserted between the folded layers of the tube component and immediately adjacent the folded edge. The elastic component and the folded tube component layers are straight stitched together from the front end along a distance of 60 mm toward the lateral centerline of the leg band. Similarly, the elastic and folded tube components are straight stitched from the back end along a distance of 40 mm toward the lateral centerline of the leg band. These are preliminary stitches to deaden the ends at zero strain. The rest of the elastic will be stretched as it is serged.

The fabric tube components of the front waist band are cut to a length of 260 mm. Each waist band fabric tube layer is folded in half along its longitudinal axis and pressed with a heated iron to make a crease. A 250 mm long piece of the elastic component is inserted between the folded layers of the tube component. The elastic component and the folded tube component layers are straight stitched together from each end along a distance of 45 mm toward the midpoint of the waist band. These are preliminary stitches meant to deaden the ends at zero strain.

Cut the fabric tube components of the rear waist band to a length of 305 mm. Each waist band fabric tube layer is folded in half along its longitudinal axis and pressed with a heated iron to make a crease. A 245 mm long piece of the elastic component is inserted between the folded layers of the tube component. The elastic component and the folded tube component layers are straight stitched together from each end along a distance of 40 mm toward the midpoint of the waist band. These are preliminary stitches meant to deaden the ends at zero strain.

Stretch and serge each of the leg bands and waist bands to create a sealed composite or tube. The inner liner elastic is stretched to the same dimension as the leg or waist band materials.

The right sides of the outer layer and the composite inner liner are aligned and placed face-to-face. The front waist edges of the outer layer and inner liner should be coterminous, as should the back waist edges of each layer. The longitudinal axes of each layer should be coincident. The seamed edge of the front waist band tube is inserted between the front waist edges of the outer layer and inner liner such that the elastic layer of the waist band is outside the overlapped region. The waist band tube is stretched such that the lateral ends of the waist band are conterminous with the laterally outboard edges of the waist edge. While holding the waist band under tension, the outer layer, waist band tube, and inner liner are serged together with woolly thread along the length of the waist edge such that the elastic component of the waist band is outside the serged seam. These steps are repeated with the back waist band and the leg bands.

The four outer cover ears (between the regions sewed for the waist and leg bands) are straight stitched a length of 0.125 inches around and trimmed with pinking shears to prevent buckling of the ears when the outer cover is inverted. The outer cover is inverted through the gap in the seam in the composite inner liner and the ears are pressed flat with an iron. The opening in the inner liner is straight stitched closed, turning in the 0.125 inch seam allowance.

All zigzag and straight stitch sewing in this example is done with a model Bernina 1001 sewing machine available from Bernina or a Bernina dealer. All serging is done with a Brother "Lock" 1034 D Serger machine available from Amazon.com.

Example 2 is a laundering resistant re-usable outer cover having an outer cover, left and right side leg bands, front and back waist bands, a front landing zone, two ear fastening elements adapted to fasten releasably to the landing zone, and two insert fastening elements. The outer cover forms the majority of the garment-facing surface of the article and is stretchable in the lateral direction. The outer cover comprises a tri-laminate comprising two extensible nonwovens and an elastically stretchable film sandwiched therebetween. The first extensible nonwoven forms the garment-facing side of the outer cover, while the second extensible nonwoven forms the wearer-facing side of the outer cover. In this exemplary embodiment, the first extensible nonwoven comprises a 27 gsm HEC nonwoven nonwoven (Excell Style 382D available from Fiberweb/BBA). The elastically stretchable film comprises a 27 gsm Vistamaxx film and is extrusion-bonded to the second extensible nonwoven (a 22 gsm Sofspan 200 available from Fiberweb France), forming a bilaminate. The elastically stretchable film comprises a Vistamaxx 22 gsm Vistamaxx layer and two skin layers of 5 gsm polyethylene, one skin layer on each surface of the Vistamaxx film. The entire bilaminate may be apertured. As identified in the table below, Example 2A is apertured to a depth of 0.120", Example 2B is apertured to a depth of 0.140", Example 2C is apertured to a depth of 0.160", and Example 2D is unapertured. For Examples 2A, 2B, and 2C, the entire bilaminate was apertured. For all measurements other than WVTR, the bilaminate was unapertured. In alternate embodiments, only part of the bilaminate may be apertured.

Aperturing is performed as described in co-pending U.S. patent application Ser. No. 12/534,353, filed Aug. 3, 2009 in the name of Qureshi, et al., without heating. The result of the process is a plurality of three-dimensional, conical or "volcano-shaped" apertures. The first nonwoven is adhesively bonded to the elastically stretchable film side of the bilaminate via a 0.0006 g/in$^2$ spiral Bostik 2031 adhesive. The trilaminate outer cover is then mechanically activated (i.e., incrementally stretched) using a ringrolling process. The ringroll tooth pitch is 0.100" and the depth of engagement is 0.158".

The landing zone and ear fastening elements are adapted to releasably and securely fasten to one another. The landing zone, which comprises the loop component of a hook and loop fastening system, is affixed to the outer surface of the outer cover in the front waist region longitudinally inboard from the front waistband, and separated from the waistband by a gap. The ear fastening elements are disposed on the wearer-facing surface of the outer cover in the back ear regions—i.e., the laterally distal portions of the back waist region of the outer cover—and comprise the hook component of a hook and loop fastening system mounted to a fastening support element.

The leg and waist bands are elastically stretchable, soft, and comfortable for the wearer. The leg and waist bands comprise Lycra elastic strands sandwiched between extensible nonwoven layers. The front waistband is cut to a 241 mm length×15 mm width and applied to the outer surface of the outer cover conterminous with the front waist edge of the article. The back waistband is cut to a 200 mm length×15 mm width and applied to the outer surface of the outer cover conterminous with the back waist edge of the article. The leg bands are cut to a 271 mm length×15 mm width, stretched, and applied to the outer surface of the outer cover conterminous with the back waist edge of the article. The leg and waist bands are affixed to the outer cover via 0.0006 g/in² spiral Bostik 2031 adhesive.

measurements were taken from two different Bumkins diaper covers. The two different samples were ordered from the same source in different months using the same product identifiers. Because of the disparity in the WVTR values, both values are presented separately.

Example 10 is a Stacinator So Simple diaper cover, size M, available from MLB Industries, Inc., El Cajon, Calif.

TABLE 1

Characteristics of Durable and Semi-Durable Absorbent Article Outer Covers

| Example | Outer Cover WVTR (g/m2/d) | Outer Cover Composite Extension Force (N) | | Whole Product Back Extension Test | | | Leg extension force (N) @ 85% extension |
|---|---|---|---|---|---|---|---|
| | | E50% | E100% C1/C2 | Absolute extension @ 5N force (mm) | % extension @ 5N force | Unload Force @ 25% extension (N) | |
| 1 | 7900 | 2.99 | 13.17/2.53 | 77 | 23 | 3.5 | 2.22 |
| 2 | A 1300 B 1500 C 1800 D 50 | 1.34 | 2.10/0.90 | 80 | 28 | 1.5 | 1.40 |
| 3 "Bum Genius" | 790* | 49% max (100N) | n.a. | 122 | 40 | 0.9 | 3.0 |
| 4 "gDiaper" | 6700* | 2.7 | 7.9/1.8 | 14 | 5 | 12 | 0.8 |
| 5 "Bummis SuperBrite" | 360 | 19.5 | 32.6/8.6 | 105 | 28 | 2.1 | 1.8 |
| 6 "Imse Vimse" | 910* | 14.24 | 47.54/n.a. (100N 138% max) | 136 | 40 | 1.7 | 2.56 |
| 7 "Fuzzi Bunz" | 1140* | Max 48% | n.a. | 177 | 46 | 0.4 | 2.6 |
| 8 "Diaperaps" | 900 | 10.0 | 21.3 | 119 | 43 | 0.7 | 2.3 |
| 9 "Bumkins" | 370* 1000* (Tested twice) | Max 13% | n.a. | 76 | 24 | 3.3 | 0.64 |
| 10 "Stacinator" | 480 | 16.3 | 33.8/8.5 | 110 | 50 | 0 | n.a. 38% max |

*Includes all layers of a multi-layer outer cover.

The outer cover also provides means by which an absorbent insert may be releasably affixed thereto in order to provide a complete and functional absorbent article for the wearer's use. In this embodiment, an insert fastening element comprising the loop component of a hook and loop fastening system is disposed in each of the front and back waist regions on the wearer-facing surface of the outer cover. The insert fastening element of this embodiment is approximately 50 mm wide, centered at the longitudinal centerline of the outer cover. Other sizes, shapes, and placement of the fastener are possible. Very large (in terms of area) or very thick fastening components may have an undesirable effect on the extensibility or breathability of the outer cover, and therefore the fastening element should be selected with attention to its thickness, breathability, extensibility, and strength of attachment per unit area.

Example 3 is a Bum Genius 3.0 one-size cloth diaper, available from Cotton Babies, Inc., St. Louis, Mo.

Example 4 is a gDiaper, size M, available from gDiaper, Inc., Portland, Oreg.

Example 5 is a Bummis SuperBrite diaper cover, size M, available from Bummis, Inc., Montreal, Quebec, Canada.

Example 6 is an Imse Vimse diaper cover available from Imse Vimse USA, Nashville, Tenn.

Example 7 is a Fuzzi Bunz cloth pocket diaper, size L, available from Mother of Eden, Lafayette, La.

Example 8 is a Diaperaps diaper cover, size medium, available from Diaperaps: Baby's Organic Nursery, Granada Hills, Calif.

Example 9 is a Bumkins diaper cover, size M, available from Bumkins Finer Baby Products, Scottsdale, Ariz. Two WVTR measurements are reported for Example 9. These Examples 1 and 2 are the only outer covers to have the following combinations of relevant properties:
  WVTR greater than 1200 g/m2/24 hr and Whole Product Back Extension greater than 15% at 5N
  WVTR greater than 1200 g/m2/24 hr and Whole Product Back Extension greater than 25 mm (50 mm) at 5 N
  WVTR greater than 1200 g/m2/24 hr and Whole Product Back Extension greater than 15% at 5 N and Whole Product Back Unload greater than 1.0N at 25% extension
  Whole Product Back Extension of at least 15% under an applied force of 5N and Whole Product Back Unload greater than 1.0N at 25% extension
  Whole Product Back Extension greater than 15%, or even 20%, at 5N and OC Composite Extension Force at 50% extension less than 5N Test Methods All testing was performed at 23°±2° C. and 50±2% relative humidity. All samples were equilibrated at that environment for at 2 hours before testing.

Whole Product Back Extension Forces

Whole product back extension forces are measured on a complete outer cover, including all layers, components, subcomponents, etc. Whole product back extension forces are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with 1 inch×1 inch diamond faced grips.

As used herein 00% strain means that the sample has been elongated by 200% of its original length measured under no applied load. For example, a sample with an original length of 100 mm will have a 200% strain when elongated to a length of 300 mm.

Program the tensile tester to extend the specimen to 100% strain at a rate of 254 mm/min., hold at that strain for 30 sec. and then return to 0% strain at 254 mm/min. After 60 sec. again extend the sample to 100% strain at 254 mm/min., hold for 30 sec. and then return to 0% strain at 254 mm/min. Set the data acquisition rate to 100 Hz. From the force versus % strain curve, program the software to report the extension (mm) at 5N of force on the first load cycle, the % strain (%) at 5N of force on the first load cycle, and the force (N) at 25% strain on the first unload cycle.

For a taped-type absorbent article: Set the gage length to the length 195 as shown in FIG. 1. Zero the crosshead. Insert the specimen into the upper grips, aligning the edge of the fasteners 42 that is proximal to longitudinal centerline 52 with the lower edge of the grip face and close the grips. Zero the load cell. Insert the other end of the specimen into the lower grips aligning the edge of the fasteners 42 that is proximal to longitudinal centerline 52 with the upper edge of the grip face, and close the grips. The specimen should be under enough tension to eliminate any slack in the sample, but force measured by the instrument must be less than 0.5N. Start the tensile tester's program, and record data.

For a pants-type absorbent article: Measure the waist circumference of the article. Divide the waist circumference by 2 to calculate a back waist length. Fold the article such that the front or top portion of the waist and the back or bottom portion of the waist are of equal length (i.e., the waist circumference divided by 2). Set the gage length to the back waist length. Zero the crosshead. Insert the specimen into the upper grips, aligning the edge of the waist of the folded article with the lower edge of the grip face and close the grips. Zero the load cell. Insert the other end of the specimen into the lower grips aligning the edge of the waist of the folded article with the upper edge of the grip face, and close the grips. Make a T-shaped cut longitudinally through the front waist and laterally through the crotch of the article, such that the front and rear waist portions are separated. The specimen should be under enough tension to eliminate any slack in the sample, but force measured by the instrument must be less than 0.5N. Start the tensile tester's program, and record data.

Report extension (mm) at 5N of force on the first load cycle to ±1 mm, the % strain (%) at 5N of force on the first load cycle to ±0.1%, and the force (N) at 25% strain on the first unload cycle to ±0.1 N.

Leg Force at 85% Extension

The leg force at 85% extension is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell (typically 10N). Both the movable (upper) and stationary (lower) pneumatic jaws are fitted with 1 inch×1 inch rubber faced grips. The gage length is set as 100 mm, and the data acquisition rate is set to 100 Hz.

Using scissors or a razor knife, remove the leg cuff 187 from the article, cutting immediately proximate to the seam of the leg cuff Once removed, locate the terminal edge of the elastic where it is anchored by adhesive, sewing or other means. Using a felt tipped marker, draw a line at the anchor point. Mark the other end of the leg cuff in like fashion. Extend the leg cuff to its full extension and measure its extended length between the two marks to the nearest 1 mm. Record this length as the cuff length and discard that leg cuff Calculate the extensions as follows:

$$95\% \text{ extension (mm)} = (\text{cuff length} \times 0.95) - \text{gage length}$$

$$85\% \text{ extension (mm)} = (\text{cuff length} \times 0.85) - \text{gage length}$$

Program the tensile tester to extend the specimen to 95% extension at 254 mm/min., hold at this extension for 5 sec., and return at a rate of 254 mm/min to 0% extension. Hold for an additional 5 sec. and again extend to 95% extension at 254 mm/min., hold at this extension for 5 sec. and return at a rate of 254 mm/min to 0% extension. From the force verses extension curve, program the software to report the force at 85% extension on the second return cycle.

Remove another leg cuff and mark the anchoring point as described above taking care not to extend or deform the leg cuff specimen. Set the gage length to 100 mm and zero the crosshead. Insert one end of the leg cuff into the top grip, aligning the bottom edge of the grip face with the mark at the anchoring point, and close the grip face. Zero the load cell. Insert the other end of the leg cuff into the bottom grip, aligning the top edge of the grip face with the mark at the anchoring point, and close the grip face. Start the tensile tester's program and collect data.

Report the force (N) at 85% extension from the second unload cycle to ±0.01 N.

Outer Cover Composite Extension Force

The Outer Cover Composite Extension Forces are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips wider than the width of the specimen. The gage length is 25.4 mm and the data acquisition rate is 100 Hz.

Program the tensile tester to extend the specimen to 110% strain at a crosshead speed of 254 mm/min. and then return to the original crosshead position. Program the software to report the force (N) at 50% strain and 100% strain.

Using a JDC precision cutter (Thwing Albert) cut along the longitudinal axis of the outer cover a 1" wide strip in the longitudinal direction of the outer cover that is 3" long. If there are multiple layers of the outer cover the specimen should be cut though all layers. The composite should be tested as a whole and also as the individual layers. Any single specimen (either composite or single layer) should only be tested once.

Set the gage length to 25.4 mm, zero the crosshead and zero the load cell. Insert the specimen into the upper grips, aligning it vertically within the upper and lower jaws and close the upper grips. Insert the specimen into the lower grips and close. The specimen should be under enough tension to eliminate any slack, but less than 0.05N of force on the load cell. Start the tensile tester's program and collect data.

Report the force (N) at 50% extension for the composite (multi-layered) specimen to ±0.01 N. Report the force (N) at 100% extension for each of the single layered specimens to ±0.01 N.

Water Vapor Transmission Rate

Water Vapor Transmission rate (WVTR) is measured according to EDANA/INDA Worldwide Strategic Partners Method WSP 70.4 (08) using a Permatran-W model 100K (MOCON, Minnesota, MN). The test method was run as per the WSP standard test, using a test apparatus temperature of 37.8 C, a nitrogen flowrate of 120 SCCM, and the standard mode with 2 cycles and 5 minute exam time. Each cell is individually adjusted to a relative humidity (RH) of 60%±1.5%. The standard reference film (S/N 1008WK089 from MOCON) should be run prior to testing the samples in order to ensure that the equipment is running properly. The standard reference film results should be within ±10% of the values reported by MOCON.

Using scissors or a die cut a specimen 35 mm in diameter. If the outer cover is multilayered the specimen is run as the composite sample. The side of the outer cover which normally faces the skin is oriented toward the water for testing. Report the WVTR as $g/m^2/24$ hr to the nearest 1 $g/m^2/24$ hr.

Simple Tensile Test for Force Wall

The materials of this invention when pulled in a Tensile Test show two distinct regions: the first region in which the main contribution to the force is from the elastic portion of the laminate and a second region in which the force contribution from the inelastic portion of the laminate starts becoming significant. In the force versus strain curve, the second region has a significantly higher slope compared to the first region. The percent strain at which this change in slope occurs is referred to as the Force Wall.

The Simple Tensile Test for Force Wall and also the Hysteresis Test to follow utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select a sample that is 7.62 cm long and 1.5 cm wide, with the long dimension being in the direction of stretch. If a waist or leg band sample is taken from a product, the width of the sample should be the entire width of the waist or the leg band. In some cases, if it is not be possible to get a 7.62 cm long sample, a smaller sample may be used, but a gage length of 25 mm must still be used.
2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.
3. Calibrate the tester according to the manufacturer's instructions.
4. Set the distance between the grips at 25 mm.
5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.
6. Pull the sample at a constant cross head speed of 254 mm/min to 1000% strain (i.e., 11× the $l_{ini}$), or until the sample breaks.
7. The computer records the force exerted on the sample during the test as a function of applied strain.
8. Plot force (N/cm) versus percent strain and measure the force wall as the strain at which the slope of the force vs. strain curve increases sharply. This can either be done manually or using the software of the tensile tester.
9. Perform 5 repetitions on each sample and report average and standard deviation.

Hysteresis Test

Steps 1 to 5 are same as for the Force Wall Test.

6(a). First cycle loading: Pull the sample to the force wall at a constant cross head speed of 254 mm/min. The force wall is determined first as described in the Simple Tensile Test above. At the force wall, report the stretched sample length between the jaws as $l_{max}$.

6(b). First cycle unloading: Hold the sample at the force wall strain for 30 seconds and then return the crosshead to its starting position (0% strain) at a constant cross head speed of 254 mm/min. Hold the sample in the unstrained state for 1 minute.

6(c). Second cycle loading: Pull the sample to the force wall at a constant cross head speed of 254 mm/min.

6(d). Second cycle unload: Next, return the crosshead to its starting position (i.e. 0% strain) at a constant cross head speed of 254 mm/min.

A computer data system records the force exerted on the sample during the test as a function of applied strain. From the resulting data generated, the following quantities are reported (note that loads are reported as force divided by the width of the sample and do not take into account the thickness of the sample):

1. First cycle load force and percent strain at the force wall (N/cm).
2. First cycle unload force at a strain that is 15% of the strain at the force wall. (For example, if the force wall is at 200%, unload is measured at 30% strain).
3. % set: Record length of sample at a second cycle load force of 0.02 N/cm ($l_{ext}$). Calculate % set as the strain measured at a second cycle load of 0.02N/cm reported as a percent of the strain at the force wall)

$$\% \text{ set} = (l_{ext} - l_{ini})/(l_{max} - l_{ini}) * 100\%.$$

Five repetitions are done on each sample and the average and standard deviation reported.

Modified AATCC Test Method 124-2001

In a wash cycle, a component of an absorbent article, such as an outer cover, is machine washed and machine dried according to the protocol from AATCC (American Association of Textile Chemists and Colorists) Test Method 124-2001, with the selected parameters and variations listed below.

a) Per section 6, Apparatus and materials, a Kenmore 600 (Heavy Duty—Super Capacity Plus—Quiet Pak) is used for the automatic washing machine, and a Maytag Commercial (such as model numbers MDE27MNACW, MDE15MNAYW, and MDE13MNACW) is used for the automatic tumble dryer.

b) Despite the instructions in Section 6, Apparatus and materials, the following ballast is used: Test Fabric style 493 from Testfabrics, Inc, West Pittston, Pa., which is cotton sheeting, with a thread count of 60×60, a weight of 151 gsm, and a size of 55' by 39".

c) Despite the instructions in Section 6, Apparatus and materials, the evaluation area is not configured according to section 6.7 and the apparatus of section 6.8 is not used. Instead, all visual evaluations are preformed under typical artificial lighting conditions (e.g. fluorescent light), which allows a person with normal vision to clearly see.

d) Despite the instructions in Section 7, Test Specimen, the component to be tested is (as necessary) entirely removed from the rest of the absorbent article, and (to the extent allowed by the removal) the component is tested as an undamaged whole. Up to three components of the same type are washed simultaneously.

e) Regarding the machine wash in Section 8.2.2, use the "large" setting on the machine for the water level, select a wash temperature of 32+/−3° C. (90+/−5° F.), and a rinse temperature of 16+/−3° C. (60+/−5° F.).

f) Regarding the settings in Section 8.2.2, select Normal/Cotton Sturdy, which has a washing time of 12 minutes, an initial spin time of 6 minutes, a refill time of 4 minutes, a rinse time of 5 minutes, and a final spin cycle time of 6 minutes.

g) Regarding the Drying in Section 8.3, select Cotton Sturdy and Whites & Colors.

h) Despite the instructions in Section 8.5, the steps of conditioning and preconditioning are not performed.

i) Despite the instructions in Section 9, Evaluation, these evaluation steps are not performed. Instead, the tested component is evaluated by one of skill in the art, to determine whether the testing has resulted in significant degradation to the appearance or performance of the article that would render it unsuitable for its intended functionality and/or use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A reusable outer cover configured to attach to a disposable absorbent insert, wherein the reusable outer cover has a front region, a back region, and a crotch region disposed longitudinally between the front region and the back region, and a wearer-facing surface disposed opposite a garment-facing surface, the reusable outer cover comprising:
    an inner layer defining the wearer-facing surface of the outer cover and an outer layer defining the garment-facing surface of the outer cover;
    wherein the inner layer is apertured;
    an insert attachment point on the inner layer configured to attach to a portion of the disposable absorbent insert;
    a first longitudinally extending edge and a second longitudinally extending edge laterally spaced from the first longitudinally extending edge;
    a first elastic leg band adjacent the first longitudinally extending edge;
    a second elastic leg band adjacent the second longitudinally extending edge;
    a first laterally extending edge and a second laterally extending edge longitudinally spaced from the first laterally extending edge;
    a first elastic waist band adjacent the first lateral end edge;
    a second elastic waist band adjacent the second lateral end edge;
    a first side panel having a distal end portion extending laterally outward from the first longitudinally extending edge;
    a second side panel having a distal end portion extending laterally outward from the second longitudinally extending edge;
    a landing zone in the front region, wherein a portion of the first side panel and a portion of the second side panel are configured to be joined to the landing zone; and
    an anchoring band attached to at least one of the inner layer and the outer layer at two or more attachment points between the first and second side panels proximate a laterally extending edge corresponding to the back region of the absorbent article, wherein the anchoring band is free to move relative to the inner and outer layers between the attachment points;
    wherein the outer cover has a WVTR of at least 1,200 g/m$^2$/24 hr and a Whole Product Back Extension of at least 15% under an applied force of 5N.

2. The outer cover of claim 1, wherein the outer layer is apertured.

3. The outer cover of claim 1, wherein the inner layer has a higher modulus of elasticity than the outer layer.

4. The outer cover of claim 1, wherein the inner layer is hydrophobic.

5. The outer cover of claim 4, wherein the inner layer and the outer layer are hydrophobic, and wherein the inner layer is more hydrophobic than the outer layer.

6. The outer cover of claim 1, wherein the outer layer is a woven fabric.

7. The outer cover of claim 1, wherein the outer layer is made from a material selected from the group consisting of cotton, wool, bamboo, hemp, silk, rayon, polyester, nylon, Lycra, Spandex, breathable waterproof materials with microscopic pores smaller than a water droplet but larger than a water vapor molecule, fabrics comprising microencapsulated phase-change polymer materials, fiber-based moisture wicking systems, and combinations thereof.

8. The outer cover of claim 1, wherein the outer layer has a basis weight from 0.09-0.15 gram/in$^2$.

9. An absorbent article comprising:
    the reusable outer cover of claim 1; and
    a disposable absorbent insert comprising:
        a self-contained absorbent assembly comprising:
            a fluid impermeable layer; and
            a gasketing system.

10. The absorbent article of claim 9, wherein a portion of a garment-facing surface of the disposable absorbent insert is configured to be attached to the insert attachment point.

11. The outer cover of claim 1, wherein the outer cover has a WVTR of at least 3000 g/m$^2$/24 hr, and wherein the outer cover is launderable.

12. The outer cover of claim 1, wherein the outer cover has a WVTR of less than 15,000 g/m²/24 hr, and wherein the outer cover is laundering resistant.

13. The outer cover of claim 1, wherein the outer cover has a WVTR of less than 10,000 g/m²/24 hr.

14. The outer cover of claim 1, wherein the outer cover has a Whole Product Back Extension of less than 100 mm under an applied force of 5N.

15. The outer cover of claim 1, wherein the outer cover has an unload force of at least 1.0N at 25% extension in the Whole Product Back Extension test.

16. The outer cover of claim 1, wherein the outer cover has an unload force of at least 2.0N at 25% extension in the Whole Product Back Extension test.

17. The outer cover of claim 1, comprising a second insert attachment point on the inner layer configured to attach to a second portion of the disposable absorbent insert.

18. The outer cover of claim 17, wherein the insert attachment point is positioned in the front region, and wherein the second insert attachment point is positioned in the back region.

19. A reusable outer cover configured to attach to a disposable absorbent insert, wherein the reusable outer cover has a front region, a back region, and a crotch region disposed longitudinally between the front region and the back region, and a wearer-facing surface disposed opposite a garment-facing surface, the reusable outer cover comprising:
   an inner layer defining the wearer-facing surface of the outer cover and an outer layer defining the garment-facing surface of the outer cover;
   wherein the inner layer and the outer layer are apertured;
   an insert attachment point on the inner layer configured to attach to a portion of the disposable absorbent insert;
   a first longitudinally extending edge and a second longitudinally extending edge laterally spaced from the first longitudinally extending edge;
   a first elastic leg band adjacent the first longitudinally extending edge;
   a second elastic leg band adjacent the second longitudinally extending edge;
   a first laterally extending edge and a second laterally extending edge longitudinally spaced from the first laterally extending edge;
   a first elastic waist band adjacent the first lateral end edge;
   a second elastic waist band adjacent the second lateral end edge;
   a first side panel having a distal end portion extending laterally outward from the first longitudinally extending edge;
   a second side panel having a distal end portion extending laterally outward from the second longitudinally extending edge;
   a landing zone in the front region, wherein a portion of the first side panel and a portion of the second side panel are configured to be joined to the landing zone; and
   an anchoring band attached to at least one of the inner layer and the outer layer at two or more attachment points between the first and second side panels proximate a laterally extending edge corresponding to the back region of the absorbent article, wherein the anchoring band is free to move relative to the inner and outer layers between the attachment points;
   wherein the outer cover has a WVTR of at least 1200 g/m²/24 hr and a Whole Product Back Extension of at least 15% under an applied force of 5N.

20. A reusable outer cover configured to attach to a disposable absorbent insert, wherein the reusable outer cover has a front region, a back region, and a crotch region disposed longitudinally between the front region and the back region, and a wearer-facing surface disposed opposite a garment-facing surface, the reusable outer cover comprising:
   an inner layer defining the wearer-facing surface of the outer cover and an outer layer defining the garment-facing surface of the outer cover;
   wherein the inner layer is apertured;
   first and second insert attachment points on the inner layer, each configured to attach to a portion of the disposable absorbent insert;
   a first longitudinally extending edge and a second longitudinally extending edge laterally spaced from the first longitudinally extending edge;
   a first elastic leg band adjacent the first longitudinally extending edge;
   a second elastic leg band adjacent the second longitudinally extending edge;
   a first laterally extending edge and a second laterally extending edge longitudinally spaced from the first laterally extending edge;
   a first elastic waist band adjacent the first lateral end edge;
   a second elastic waist band adjacent the second lateral end edge;
   an anchoring band attached to at least one of the inner layer and the outer layer at two or more attachment points between the first and second side panels proximate a laterally extending edge corresponding to the back region of the absorbent article, wherein the anchoring band is free to move relative to the inner and outer layers between the attachment points;
   wherein the outer cover has a WVTR of at least 1200 g/m²/24 hr and a Whole Product Back Extension of at least 15% under an applied force of 5N.

* * * * *